（12）United States Patent
Ahmed et al.

(10) Patent No.: US 11,998,014 B1
(45) Date of Patent: Jun. 4, 2024

(54) O-{1-[(3,5-DINITROBENZOYL)AMINO]PROPAN-2-YL} (4-CHLOROPHENYL)CARBAMOTHIOATE AS AN ECO-FRIENDLY INSECTICIDAL AGENT AGAINST *SPODOPTERA LITTORALIS* (BOISD.)

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Mohamed Gouda, Al-Ahsa (SA); Antar Ahmed Abdelhamid Ahmed, Sohag (EG); Mohamed A. Gad, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/403,049

(22) Filed: Jan. 3, 2024

(51) Int. Cl.
*C07C 333/08* (2006.01)
*A01N 47/20* (2006.01)
*A01P 7/04* (2006.01)
*A01P 17/00* (2006.01)
*A61P 7/04* (2006.01)
*A61P 17/00* (2006.01)

(52) U.S. Cl.
CPC ............... *A01N 47/20* (2013.01); *A01P 7/04* (2021.08); *A01P 17/00* (2021.08); *C07C 333/08* (2013.01)

(58) Field of Classification Search
CPC ......... C07C 333/08; A01N 47/20; A01P 7/04; A01P 17/00
See application file for complete search history.

(56) References Cited

U.S. PATENT DOCUMENTS 9,781,935 B2   10/2017   Heemstra et al.
10,258,045 B2   4/2019   Heemstra et al.

FOREIGN PATENT DOCUMENTS

EP            396406 A1      3/2022

OTHER PUBLICATIONS

PubChem, Nat. Lib. Of Med., CID 9269599, publ. Jul. 30, 2006, pp. 1-9 (Year: 2006).*
Spallarossa A, Cesarini S, Ranise A, Bruno O, Schenone S, La Colla P, Collu G, Sanna G, Secci B, Loddo R. "Novel modifications in the series of O-(2-phthalimidoethyl)-N-substituted thiocarbamates and their ring-opened congeners as non-nucleoside HIV-1 reverse transcriptase inhibitors". Eur J Med Chem. Apr. 2009;44(4):1650-63.

* cited by examiner

*Primary Examiner* — Sarah Pihonak
(74) *Attorney, Agent, or Firm* — Nath, Goldberg & Meyer; Richard C. Litman

(57) ABSTRACT

Synthesis of a compound O-{1-[(3,5-dinitrobenzoyl)amino]propan-2-yl} (4-chlorophenyl)carbamothioate and its use as an insecticidal agent.

20 Claims, No Drawings

O-{1-[(3,5-DINITROBENZOYL)AMINO]PROPAN-2-YL} (4-CHLOROPHENYL)CARBAMOTHIOATE AS AN ECO-FRIENDLY INSECTICIDAL AGENT AGAINST *SPODOPTERA LITTORALIS* (BOISD.)

BACKGROUND

1. Field

The present disclosure relates to synthesis of the compound O-{1-[(3,5-dinitrobenzoyl)amino]propan-2-yl} (4-chlorophenyl)carbamothioate and its use as an insecticidal agent.

2. Description of the Related Art

According to the majority of problems brought on by the use of pesticides, the use of safe and distinctively tailored organic components is necessary for development in order to decrease the effects of pesticide compounds. Juvenile hormone analogues as an example of insect growth regulators may be promising due to their defined mechanism of action on pests and lower poisonousness towards vertebrates than traditional insecticides. As a result, a special collection of pure insect growth regulators has been created.

Insect growth regulators (IGRs) are third-generation insecticides less toxic and compatible with insect pest management that were developed to reduce the pollution of food and environment. These compounds have a specific mode of action on insects and a lower toxicity against vertebrates than conventional insecticides for this purpose, the endocrine system of insects has been intentionally targeted for insecticidal activity. The developed insecticides are used to suppress insect populations, stopping their proliferation by disrupting their normal endocrine functions. Juvenile hormone mimics (e.g., methoprene (1), fenoxycarb (2)), anti-juvenile hormones (e.g., precocene II), and ecdysone analogs (e.g., tebufenozide (3)) are some examples illustrated below:

Other IGR compounds such as teflubenzuron and hexaflumuron act preferentially by interfering with the chitin synthesis metabolism (chitin synthesis inhibitors). These substances appear to have a high target pest specificity and their effects can differ significantly among insect species. Some IGRs are considered highly toxic ($LC_{50}$ 100-1000 mg/L for tebufenozide) to very highly toxic ($LC_{50}$<100 mg/L for fenoxycarb and methoprene) for aquatic insects. Endocrine-disrupting compounds (EDCs) is a term commonly used to describe these substances that potentially interfere with hormones. Until now, observations on the impact of EDCs mainly focused on vertebrates and steroid substances. Endocrine disruption has also been relatively well studied in aquatic invertebrates but hardly any information is available on soil invertebrates. Studies on the toxicity of IGRs are mainly conducted by chemical companies producing or marketing the product or with their financial support and focused principally on target pest organisms.

Thus, new insecticides and/or pesticides solving the aforementioned problems using green chemistry methods are desired.

SUMMARY

The present subject matter relates to the synthesis of a unique pure insect growth regulator, as well as the regulator itself. The structure of this synthesized compound, which is related to the most well-known insect growth regulator insecticides, can be confirmed by elemental and contemporary spectroscopic investigations (IR, UV, $^1$HNMR, $^{13}$CNMR, and elemental analysis). The target compound O-{1-[(3,5-dinitrobenzoyl)amino]propan-2-yl} (4-chlorophenyl)carbamothioate (2) can be synthesized by the reaction of N-(2-hydroxypropyl)-3,5-dinitrobenzamide with 4-chlorophenyl isothiocyanate and 1,4-dioxane in high yields. The insecticidal efficacy of the chemically newly synthesized compound was checked against *Spodoptera littoralis* under laboratory conditions and compared with Fenoxycarb as a reference insecticide. It has been found that the present compound has a $LC_{50}$=12.505 mg/L, whereas Fenoxycarb has a $LC_{50}$=5.943 mg/L, indicating the insecticidal effectiveness of the present compound.

In an embodiment, the present subject matter relates to compositions containing, processes for making, and methods of using a O-{1-[(3,5-dinitrobenzoyl)amino]propan-2-yl} (4-chlorophenyl)carbamothioate compound having the formula I:

In another embodiment, the present subject matter relates to the use of an insecticidally acceptable composition comprising an insecticidally effective amount of the O-{1-[(3,5-dinitrobenzoyl)amino]propan-2-yl} (4-chlorophenyl)carbamothioate compound and an insecticidally acceptable carrier.

In a further embodiment, the present subject matter relates to a method of killing insects comprising applying to said insects or to a target site of insect infestation an insecticidally effective amount of the O-{1-[(3,5-dinitrobenzoyl)amino]propan-2-yl} (4-chlorophenyl)carbamothioate compound.

In an additional embodiment, the present subject matter relates to a method of repelling insects comprising applying to a target site of insect infestation an insect repelling effective amount of the O-{1-[(3,5-dinitrobenzoyl)amino]propan-2-yl} (4-chlorophenyl)carbamothioate compound.

In one more embodiment, the present subject matter relates to a method of controlling an insect pest comprising applying to a target site of insect infestation an insect controlling effective amount of the O-{1-[(3,5-dinitrobenzoyl)amino]propan-2-yl} (4-chlorophenyl)carbamothioate compound.

In a further embodiment, the present subject matter relates to a method of making the O-{1-[(3,5-dinitrobenzoyl)amino]propan-2-yl} (4-chlorophenyl)carbamothioate compound, the method comprising: mixing N-(2-hydroxypropyl)-3,5-dinitrobenzamide with 4-chlorophenyl isothiocyanate to obtain a reaction mixture; refluxing the reaction mixture with 1,4-dioxane and (Triethylamine) TEA to obtain a precipitate; filtering and recrystallizing the precipitate; and obtaining the O-{1-[(3,5-dinitrobenzoyl)amino]propan-2-yl} (4-chlorophenyl)carbamothioate compound.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the synthesis of a unique pure insect growth regulator, as well as the regulator itself. The structure of this synthesized compound, which is related to the most well-known insect growth regulator insecticides, can be confirmed by elemental and contemporary spectroscopic investigations (IR, UV, $^1$HNMR, $^{13}$CNMR, and elemental analysis). The insecticidal efficacy of the chemically newly synthesized compound was checked against *Spodoptera littoralis* under laboratory conditions and compared with Fenoxycarb as a reference insecticide. It has been found that the present compound has a $LC_{50}=12.505$ mg/L, whereas Fenoxycarb has a $LC_{50}=5.943$ mg/L, indicating the insecticidal effectiveness of the present compound.

In an embodiment, the present subject matter relates to compositions containing, processes for making, and methods of using a O-{1-[(3,5-dinitrobenzoyl)amino]propan-2-yl} (4-chlorophenyl)carbamothioate compound having the formula I:

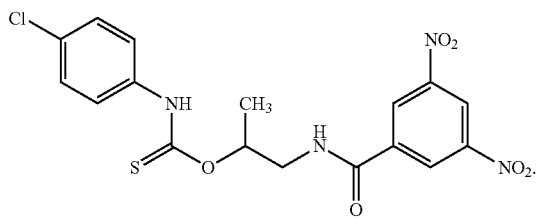

In certain embodiments, the O-{1-[(3,5-dinitrobenzoyl)amino]propan-2-yl} (4-chlorophenyl)carbamothioate compound can have a melting point of about 213° C. to about 215° ° C.

In other embodiments, the O-{1-[(3,5-dinitrobenzoyl)amino]propan-2-yl} (4-chlorophenyl)carbamothioate compound can be a white powder.

In additional embodiments, the O-{1-[(3,5-dinitrobenzoyl)amino]propan-2-yl} (4-chlorophenyl)carbamothioate compound is considered as an insect growth regulator (IGR). Accordingly, the present compound is capable of inhibiting the life cycle of an insect.

In another embodiment, the present subject matter relates to an insecticidally acceptable composition comprising an insecticidally effective amount of the O-{1-[(3,5-dinitrobenzoyl)amino]propan-2-yl} (4-chlorophenyl)carbamothioate compound and an insecticidally acceptable carrier.

In some embodiments, the present compositions and methods of use can be used for combination treatment, where other insecticidal ingredients can be included therein, or can be co-administered therewith.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art.

The present compounds are typically administered at an insecticidally effective dosage, e.g., a dosage sufficient to provide a desired activity against insects.

While the insecticidal dosage experimental levels have yet to be optimized for the present compounds, generally, each treatment of the present compositions could be expected to include from about 12.5 ppm to about 200 ppm, or mg/L, of the present compounds. In this regard, compositions having concentrations of the present compounds of about 200 ppm, about 100 ppm, about 50 ppm, about 25 ppm, or about 12.5 ppm, or mg/L, per application to a desired area of treatment are included within the present subject matter. The precise effective amount will vary from treatment to treatment and will depend upon the target area of application, the insect species being treated for, the number of insects present, and the like. The treatment area may be administered as many doses as is required to produce an effective treatment.

Liquid compositions can, for example, be prepared by dissolving, dispersing, etc. the active compound as defined above and optional adjuvants in a carrier, such as, for example, water, saline, aqueous dextrose, glycerol, glycols, ethanol, and the like, to thereby form a solution or suspension. If desired, the composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

In a further embodiment, the present subject matter relates to a method of killing insects comprising applying to said insects or to a target site of insect infestation an insecticidally effective amount of the O-{1-[(3,5-dinitrobenzoyl)amino]propan-2-yl} (4-chlorophenyl)carbamothioate compound and/or a composition containing the same.

In an embodiment, the present methods of killing insects can be effective against insects belonging to a species *Spodoptera littoralis* (Boisd.). Further, the present compound can be considered as an insect growth regulator (IGR) that inhibits the life cycle of an insect, particularly *Spodoptera littoralis*. Accordingly, the present compound can be used as an insecticide to control populations of harmful insect pests, including, by way of non-limiting example, cockroaches and fleas.

Unlike classic insecticides, the present compound is unlikely to affect an insect's nervous system and is thus more friendly to "worker insects" within closed environments. The present compound can also be more compatible with pest management systems that use biological controls. In addition, while insects can become resistant to insecticides, they are less likely to become resistant to the present compound.

In another embodiment, in the present methods of killing insects, the O-{1-[(3,5-dinitrobenzoyl)amino]propan-2-yl} (4-chlorophenyl)carbamothioate compound can have an $LC_{50}$ of about 12.505 mg/L against the species *Spodoptera littoralis* after 72 hours of treatment. In this regard, in the present methods of killing insects, the O-{1-[(3,5-dinitrobenzoyl)amino]propan-2-yl} (4-chlorophenyl)carbamothioate compound can have an $LC_{50}$ of about 12.505 mg/L against $2^{nd}$ instars of larvae of the species *Spodoptera littoralis* after 72 hours of treatment.

Similarly, in the present methods of killing insects, the O-{1-[(3,5-dinitrobenzoyl)amino]propan-2-yl} (4-chlorophenyl)carbamothioate compound can have an $LC_{50}$ of about 67.908 mg/L against the species *Spodoptera littoralis* after 72 hours of treatment. In this regard, in the present methods of killing insects, the O-{1-[(3,5-dinitrobenzoyl)amino]propan-2-yl} (4-chlorophenyl)carbamothioate compound can have an $LC_{50}$ of about 67.908 mg/L or ppm against 4th instars of larvae of the species *Spodoptera littoralis* after 72 hours of treatment.

In a further embodiment of the present methods, the O-{1-[(3,5-dinitrobenzoyl)amino]propan-2-yl} (4-chlorophenyl)carbamothioate compound can be applied to castor leaves.

In an additional embodiment of the present methods, about 12.5 to about 200 ppm of the O-{1-[(3,5-dinitrobenzoyl)amino]propan-2-yl} (4-chlorophenyl)carbamothioate compound can be applied to the insects or to the target site. In this regard, about 200 ppm, about 100 ppm, about 50 ppm, about 25 ppm, or about 12.5 ppm, or mg/L, per application of the O-{1-[(3,5-dinitrobenzoyl)amino]propan-2-yl} (4-chlorophenyl)carbamothioate compound can be applied to a desired area of treatment.

In an additional embodiment, the present subject matter relates to a method of repelling insects comprising applying to a target site of insect infestation an insect repelling effective amount of the O-{1-[(3,5-dinitrobenzoyl)amino] propan-2-yl} (4-chlorophenyl)carbamothioate compound and/or a composition containing the same.

In an embodiment, the present methods of repelling insects can be effective against insects belonging to a species *Spodoptera littoralis* or *Spodoptera littoralis* (Boisd.).

In one more embodiment, the present subject matter relates to a method of controlling an insect pest comprising applying to a target site of insect infestation an insect controlling effective amount of the O-{1-[(3,5-dinitrobenzoyl)amino]propan-2-yl} (4-chlorophenyl)carbamothioate compound.

In an embodiment, the present methods of controlling insect pests can be effective against insects belonging to a species *Spodoptera littoralis* or *Spodoptera littoralis* (Boisd.).

In some embodiments, the present subject matter relates to a method of making the O-{1-[(3,5-dinitrobenzoyl) amino]propan-2-yl} (4-chlorophenyl)carbamothioate that is a two step process. The process begins with refluxing and stirring 1-amino-3-propanol, 3,5-dintrobenzoyl chloride and (Triethylamine) TEA for at least about 3 hours to give a precipitate. The precipitate is filtered, washed, and purified to give N-(2-hydroxypropyl)-3,5-dinitrobenzamide 1 according to Scheme 1.

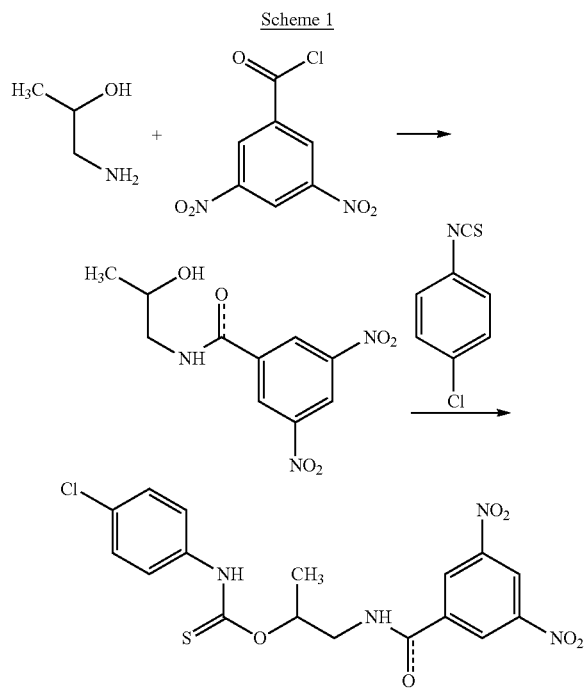

Scheme 1

The final step of the synthesis of O-{1-[(3,5-dinitrobenzoyl)amino]propan-2-yl} (4-chlorophenyl)carbamothioate includes: mixing N-(2-hydroxypropyl)-3,5-dinitrobenzamide with 4-chlorophenyl isothiocyanate to obtain a reaction mixture; refluxing the reaction mixture with 1,4-dioxane and (Triethylamine) TEA to obtain a precipitate; filtering and recrystallizing the precipitate; and obtaining the O-{1-[(3,5-dinitrobenzoyl)amino]propan-2-yl} (4-chlorophenyl)carbamothioate compound as illustrated in Scheme 1 above.

In certain embodiments, the O-{1-[(3,5-dinitrobenzoyl) amino]propan-2-yl} (4-chlorophenyl)carbamothioate compound may be obtained as a white powder. The O-{1-[(3, 5-dinitrobenzoyl)amino]propan-2-yl} (4-chlorophenyl) carbamothioate compound may be obtained in an about 67% yield.

In other embodiments, the precipitate may be washed after filtration.

In additional embodiments of the present production methods, the precipitate can be recrystallized from ethanol.

In some embodiments, two drops of TEA are added to the reaction mixture. In other embodiments, the TEA serves as a catalyst for the reaction.

The following examples relate to various methods of manufacturing certain specific compounds and application results as described herein. All compound numbers expressed herein are with reference to the synthetic pathway figures shown above.

EXAMPLES

Example 1

Preparation of
N-(2-hydroxypropyl)-3,5-dinitrobenzamide (1)

1-amino-3-propanol (1 mmol), 3,5-dintrobenzoyl chloride and drops of (Triethylamine) TEA were stirred and refluxed at ambient temperature for 3 hours to give a precipitate. The precipitate was filtered off and recrystallized from 1,4-dioxane. The precipitating product was collected by filtration, washed thoroughly, and purified via crystallization from an ethanol/dichloromethane mixture (1:1) to obtain N-(2-hydroxypropyl)-3,5-dinitrobenzamide.

Example 2

Preparation of O-{1-[(3,5-dinitrobenzoyl)amino]
propan-2-yl} (4-chlorophenyl)carbamothioate (2)

N-(2-hydroxypropyl)-3,5-dinitrobenzamide was mixed with 4-chlorophenyl isothiocyanate. The solution was then refluxed with 1,4-dioxane and two drops of (Triethylamine) TEA as a catalyst. The reaction gave a precipitate which was filtered off and crystallized from ethanol to obtain O-{1-[(3, 5-dinitrobenzoyl)amino]propan-2-yl} (4-chlorophenyl)carbamothioate (2).

Characterization data of O-{1-[(3,5-dinitrobenzoyl) amino]propan-2-yl} (4-chlorophenyl)carbamothioate (2):

White powder, yield: 67%; MP: 213-215° C. IR (v) (KBr) cm$^{-1}$: 3211 (NH), 3042(C—H $_{Aromatic}$), 2983(C—H aliphatic), 1631, (C=O). $^1$HNMR (DMSO-d$_6$): δ10.98 (s, 1H, NH), 8.44 (s, 1H, NH), 7.14-7.90 (m, 7H Ar—H), 4.52 (s, 2H, CH$_2$), 3.56 (s, 1H, CH), 1.3 (s, 3H, CH$_3$). $^{13}$C NMR (DMSO-d$_6$): δ188.02, 180.17, 165.80, 138.60, 133.83, 129.05, 128.72, 124.86, 124.11, 122.29, 60.22, 42.77, 14.74. Elemental analysis calculated for C$_{17}$H$_{15}$ClN$_4$O$_6$S (%) Calcd./found; C: 46.53/46.52, H: 3.45/3.43, N:12.77/12.75.

Example 3

Insecticidal Bioassay Screening

Five concentrations (200, 100, 50, 25, 12.5 ppm) were designed for this synthetic compound and the reference fenoxycarb's compound as the dynamic ingredients based on ppm via diluting the commercial formulation.

In this experiment, the synthetic compound was tested for its insecticidal bioactivity using the industry-standard leaf dip bioassay techniques. Preparation of the compound stocks to create 1000 ppm, 0.1 g of compounds 2 were dissolved in five mL of Dimethyl formamide & combined with 5 mL of distilled water. Until usage, the stocks were kept in a refrigerator. The target substance test results were noted & the concentrations needed to destroy 50% ($LC_{50}$) of *S. littoralis* larvae were calculated. The target compound was employed in five different concentrations, and 0.1% Tween 80 was employed as a surfactant. Castor bean leaf discs (nine centimeters in diameter) were dipped in the concentration under test for ten seconds, then fed to $2^{th}$ and $4^{th}$ larvae, which were roughly the same size and housed in glass jars (five pound). Each action carried out 3 times with ten larvae each. The mortality equalized via Abbott's formula. Calculations of mortality setback line were measurably rummage via probity analysis. Harmfulness index was strongminded via sun equations. The mortality results of larval insect were estimated through employing probit analysis through a statistics (LDP-line) equation which estimate the $LC_{50}$ values with 95% fiducially limits of lower, upper confidence limit and slope. The results of the bioassay screening can be observed in Table 1, below.

TABLE 1

Insecticidal bioeffecacy of second and fourth instars larvae of the laboratory strain of cotton leafworm, *S. littoralis* to test product (2) after 72 hours of treatment.

| | $2^{nd}$ instar larvae | | | $4^{th}$ instar larvae | | |
|---|---|---|---|---|---|---|
| Comps. | $LC_{50}$ (mg/L) at 95% | Slope | Toxicity index % | $LC_{50}$(mg/L) at 95% | Slope | Toxicity index % |
| 2 | 12.505 | 0.246 ± 0.0793 | 47.52 | 67.908 | 0.297 ± 0.0893 | 88.23 |
| fenoxycarb | 5.943 | 0.298 ± 0.0808 | 100 | 59.914 | 0.225 ± 0.0870 | 100 |

Notes:
[a]Toxicity ratio is estimated as fenoxycarb's $LC_{50}$ value for baseline toxicity/the compounds' $LC_{50}$ value * 100.

It is to be understood that the methods of making and using the O-{1-[(3,5-dinitrobenzoyl)amino]propan-2-yl} (4-chlorophenyl)carbamothioate (2) compound, and the use of compositions containing the same, are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

I

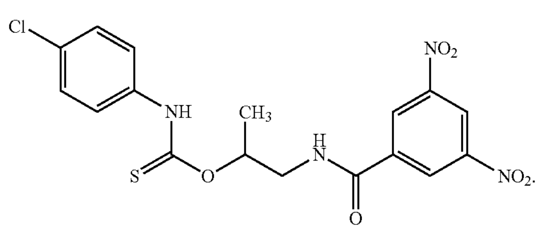

2. The compound of claim 1, wherein the melting point of the compound is about 213°C to about 215° C.

3. An insecticidally acceptable composition comprising an insecticidally effective amount of a O-{1-[(3,5-dinitrobenzoyl)amino]propan-2-yl} (4-chlorophenyl)carbamothioate compound having the formula I:

I 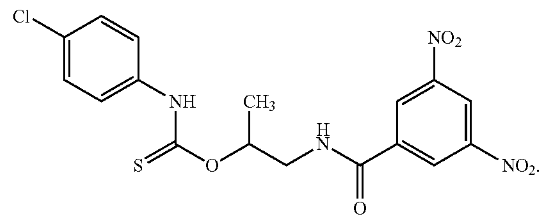 and an insecticidally acceptable carrier.

4. A method of killing insects comprising applying to said insects or to a target site of insect infestation an insecticidally effective amount of the insecticidally active composition of claim 3.

5. The method of killing insects of claim 4, wherein the insects belong to a species *Spodoptera littoralis.*

6. The method of killing insects of claim 5, wherein the O-{1-[(3,5-dinitrobenzoyl)amino]propan-2-yl} (4-chlorophenyl)carbamothioate compound has an $LC_{50}$ of about 12.505 mg/L against the species *Spodoptera littoralis* after 72 hours of treatment.

7. The method of killing insects of claim 5, wherein O-{1-[(3,5-dinitrobenzoyl)amino]propan-2-yl} (4-chlorophenyl)carbamothioate compound has an $LC_{50}$ of about 12.505 mg/L ppm against $2^{nd}$ instars of larvae of the species *Spodoptera littoralis* after 72 hours of treatment.

8. The method of killing insects of claim 5, wherein the O-{1-[(3,5-dinitrobenzoyl)amino]propan-2-yl} (4-chlorophenyl)carbamothioate compound has an $LC_{50}$ of about 67.908 mg/L against the species *Spodoptera littoralis* after 72 hours of treatment.

9. The method of killing insects of claim 5, wherein the O-{1-[(3,5-dinitrobenzoyl)amino]propan-2-yl} (4-chlorophenyl)carbamothioate compound has an $LC_{50}$ of about 67.908 mg/L ppm against $4^{th}$ instars of larvae of the species *Spodoptera littoralis* after 72 hours of treatment.

10. The method of killing insects of claim 4, wherein the O-{1-[(3,5-dinitrobenzoyl)amino]propan-2-yl} (4-chlorophenyl)carbamothioate compound is applied to castor leaves.

11. The method of killing insects of claim 4, wherein about 12.5 to about 200 ppm of the O-{1-[(3,5-dinitrobenzoyl)amino]propan-2-yl} (4-chlorophenyl)carbamothioate compound is applied to the insects or to the target site.

12. A method of repelling insects comprising applying to a target site of insect infestation an insect repelling effective amount of the insecticidally active composition of claim 3.

13. The method of repelling insects of claim 12, wherein the insects belong to a species *Spodoptera littoralis*.

14. A method of controlling an insect pest comprising applying to a target site of insect infestation an insect controlling effective amount of the insecticidally active composition of claim 3.

15. The method of controlling the insect pest of claim 14, wherein the insect pest belongs to a species *Spodoptera littoralis*.

16. A method of making a O-{1-[(3,5-dinitrobenzoyl)amino]propan-2-yl} (4-chlorophenyl)carbamothioate compound, the method comprising:
    mixing N-(2-hydroxypropyl)-3,5-dinitrobenzamide with 4-chlorophenyl isothiocyanate to obtain a reaction mixture;
    refluxing the reaction mixture with 1,4-dioxane and (Triethylamine) TEA to obtain a precipitate;
    filtering and recrystallizing the precipitate; and
    obtaining the O-{1-[(3,5-dinitrobenzoyl)amino]propan-2-yl} (4-chlorophenyl)carbamothioate compound.

17. The method of making the O-{1-[(3,5-dinitrobenzoyl)amino]propan-2-yl} (4-chlorophenyl)carbamothioate compound of claim 16, wherein the O-{1-[(3,5-dinitrobenzoyl)amino]propan-2-yl} (4-chlorophenyl)carbamothioate compound is obtained as white powder.

18. The method of making the O-{1-[(3,5-dinitrobenzoyl)amino]propan-2-yl} (4-chlorophenyl)carbamothioate compound of claim 16, wherein the compound is obtained in an about 67% yield.

19. The method of making the O-{1-[(3,5-dinitrobenzoyl)amino]propan-2-yl} (4-chlorophenyl)carbamothioate compound of claim 16, wherein the precipitate is recrystallized from ethanol.

20. The method of making the O-{1-[(3,5-dinitrobenzoyl)amino]propan-2-yl} (4-chlorophenyl)carbamothioate compound of claim 19, wherein two drops of TEA are added to the reaction mixture.

\* \* \* \* \*